United States Patent
Hussain et al.

(10) Patent No.: US 8,763,443 B2
(45) Date of Patent: Jul. 1, 2014

(54) METHOD FOR OPERATING A DENSITY MEASURING DEVICE AND DEVICE FOR DENSITY MEASUREMENT

(75) Inventors: Yousif Hussain, Weston Favell (GB); Christopher Rolph, Hartwell (GB); Tao Wang, Canterbury (GB)

(73) Assignee: Krohne AG, Basel (CH)

( * ) Notice: Subject to any disclaimer, the term of this patent is extended or adjusted under 35 U.S.C. 154(b) by 280 days.

(21) Appl. No.: 12/740,512

(22) PCT Filed: Oct. 28, 2008

(86) PCT No.: PCT/EP2008/009089
§ 371 (c)(1),
(2), (4) Date: Apr. 29, 2010

(87) PCT Pub. No.: WO2009/056270
PCT Pub. Date: May 7, 2009

(65) Prior Publication Data
US 2011/0219872 A1    Sep. 15, 2011

(30) Foreign Application Priority Data
Oct. 30, 2007  (DE) .......................... 10 2007 052 041

(51) Int. Cl.
*G01N 9/00*    (2006.01)

(52) U.S. Cl.
USPC .......................................................... 73/32 A

(58) Field of Classification Search
USPC .......................................................... 73/21 A
See application file for complete search history.

(56) References Cited

U.S. PATENT DOCUMENTS

| | | | |
|---|---|---|---|
| 4,262,523 A | 4/1981 | Stansfeld | |
| 5,827,979 A | 10/1998 | Schott et al. | |
| 6,732,570 B2 | 5/2004 | Francisco, Jr. | |
| 2002/0189323 A1 | 12/2002 | Francisco, Jr. | |
| 2005/0072236 A1* | 4/2005 | Heyman et al. | 73/602 |

FOREIGN PATENT DOCUMENTS

EP    1 426 741 A1    6/2004

* cited by examiner

*Primary Examiner* — Peter Macchiarolo
*Assistant Examiner* — Alex Devito
(74) *Attorney, Agent, or Firm* — Roberts Mlotkowski Safran & Cole, P.C.; David S. Safran

(57) ABSTRACT

A method for operating a density measuring device having a measuring tube filled with the medium for determining the density of the medium, in which the measuring tube is incited to vibrate, the frequency of the vibration determined and the density of the medium being calculated from the determined frequency and other parameters which determine the physical-geometrical properties of the measuring tube. In particular, at least one mechanical stress of the measuring tube is determined, and with the obtained mechanical stress value, the influence of the mechanical stress of the measuring tube and/or the influence of the pressure in the medium on the determined density of the medium are or is—at least partially—taken into consideration or compensated.

9 Claims, 2 Drawing Sheets

METHOD FOR OPERATING A DENSITY MEASURING DEVICE AND DEVICE FOR DENSITY MEASUREMENT

BACKGROUND OF THE INVENTION

1. Field of the Invention

The invention relates a method for operating a density measuring device having a measuring tube for determining the density of a medium, with the measuring tube being filled with the medium, the measuring tube being incited to vibrate, the frequency of the vibration being determined and the density of the medium being calculated from the determined frequency and other parameters which determine physical-geometrical properties of the measuring tube. The invention additionally relates also to a device for density measurement on the basis of vibration analysis, having at least one measuring tube, a medium which is situated in the measuring tube, at least one vibration generator which acts on the measuring tube, at least one measured value sensor for measuring the vibration of the measuring tube, and having an evaluating unit for evaluating the vibration measured by the measured value sensor and calculating a density value of the medium from the measured vibration and other parameters which determine physical-geometrical properties of the measuring tube.

2. Description of Related Art

Methods for measuring the density of a medium which is situated in a hollow body—such as, for example, in a measuring tube, in which the hollow body, whose vibration behavior is substantially known, is incited to vibrate, and the resulting vibration, in particular, the frequency of the resulting vibration, is incorporated for the determination of the density of the medium situated in the hollow body, are long known and are widely used.

Where it is referred to that the present invention relates to a method for operating a density measuring device, with the method being based on the principle of vibration analysis, this means all devices which can also be used in any case for density measurement, even if not provided primarily for density measurement. For example, it is known to also carry out a density measurement with Coriolis mass throughflow meters, with such mass throughflow measuring devices also having a measuring tube which is filled with a medium or is traversed by said medium and which is incited to vibrate, but wherein, for the determination of the mass throughput, it is not the frequency of a natural vibration which is evaluated, but primarily the phase difference between two sections of the measuring tube which is vibrating. Mass throughflow measuring devices which are based on the Coriolis principle are nonetheless fundamentally suitable for being operated in the manner of a density measuring device.

The density determination is based fundamentally on the knowledge that a mechanical system which is capable of vibration can be mathematically described in the simplest case by a simple spring-mass system, with the natural frequency of the system being in a certain functional relationship with the mass and other physical-geometrical properties of the system, such as, for example, the spring constant by means of which the relevant behavior of the spring can be mathematically depicted in the simplest case. In an idealized, purely linear spring-mass system, the natural angular frequency corresponds to the square root of the quotient of the spring constants of the spring and the overall mass of the system. If the overall mass of the system is composed, as in the case considered here, of the mass of the measuring tube and the mass of the medium situated in the measuring tube, then the contribution of the medium contained in the measuring tube to the overall mass is equal to the product of the density of the medium and the volume which is enclosed by the measuring tube and which is filled by the medium. It is directly evident that, after the determination of the frequency of the natural vibration of the hollow body—in this case of the measuring tube—by means of measurement, it is possible to determine the density of the medium enclosed by the measuring tube, assuming that the volume of the measuring tube is known.

On closer inspection, however, it has been proven in practice that the above-described modeled description of a density measuring device having a measuring tube for determining the density of a medium, with the measuring tube being filled with the medium and the measuring tube being incited to vibrate, is only a first and if appropriate insufficient modeled description of the actual conditions. It has, for example, been proven that—even for incompressible media—the density of the medium obtained from the simple approach by means of a spring-mass system also exhibits a dependency on the pressure prevailing in the measuring tube, and therefore, in the medium. It is also known that the density measurement is temperature-dependent, and specifically, to a greater extent than can be explained by a change in volume of the medium under the influence of temperature.

SUMMARY OF THE INVENTION

It is an object of the present invention to—at least partially—avoid the indicated disadvantages in known methods for operating a density measuring device and the known disadvantages of just such devices for density measurement.

The indicated object is achieved according to the invention, initially and substantially in the case of the method in question, in that at least one mechanical stress of the measuring tube is determined, and with the obtained mechanical stress value, the influence of the mechanical stress of the measuring tube and/or the influence of the pressure in the medium on the determined density of the medium are or is—at least partially—taken into consideration or compensated.

The invention is based on the knowledge that a change in the mechanical stress of the measuring tube has a manifold effect on the properties of the measuring tube, in particular specifically also on the physical-geometrical properties of the measuring tube, which, in turn, also have an effect on the determination of the density of the medium situated in the measuring tube when using simple modeled mathematical concepts.

Where it is referred to that the influence of the mechanical stress of the measuring tube and/or the influence of the pressure in the medium on the determined density of the medium is compensated, this also means that these variables which have been recognized as significant for the density determination are, in any case, also incorporated for the density determination, so that—proceeding from the simpler model concepts—correct results for the density are obtained, and consequently—with respect to the simple model concepts—the influence of mechanical stress of the measuring tube and/or the influence of the pressure in the medium is in fact "compensated" or corrected.

The influence of the mechanical stress of the measuring tube and/or the influence of the pressure in the medium on the determined density of the medium can, however, also have an immediate effect on the determination of the density of the medium, for example, by means of a more complex modeled approach, so that these variables are taken into consideration from the start and do not serve for (retroactive) correction.

According to one advantageous embodiment of the method according to the invention, the influence of the determined mechanical stress on the mechanical stiffness of the measuring tube—and therefore on the determined density of the medium—is taken into consideration or compensated. In the above-described simple spring-mass system as a model for a density measuring device with a measuring tube which is capable of vibration, the spring constant corresponds substantially to the mechanical stiffness of the measuring tube used in the density measuring device. Depending on the mathematical-physical description of a measuring tube of said type which is used, the stiffness of the measuring tube is a function of various physical and geometrical parameters of the measuring tube, for example, of the tube inner diameter and of the tube wall thickness (geometrical parameters) and the Poisson ratio and the modulus of elasticity of the material from which the measuring tube is produced (physical parameters). However, it has been proven, overall, that the mechanical stiffness of the measuring tube is also dependent on the mechanical stress which acts in the measuring tube, which can have various causes such as, for example, a stress dependency of the modulus of elasticity, or else the moments which act in a curved measuring tube which attempt to counteract the designed curves.

According to a further advantageous embodiment of the invention, the peripheral stress and/or the axial stress of the tube are or is determined as the mechanical stress. Here, the peripheral stress—which is partially also referred to as the tangential stress—acts in an axial cross section of the measuring tube wall, whereas the axial stress acts in a radial cross section of the tube wall. The normal stresses have been recognized according to the invention as being particularly significant for the determination of the density of the medium, for which reason special attention is paid to these stresses, in contrast to the tangential stresses which act in a surface.

In preferred embodiments of the invention, the mechanical stress of interest is determined by measurements obtained using at least one strain gauge strip which is preferably attached to the surface of the measuring tube which is to be measured, and in its measuring direction, indicates expansions or contractions of the supporting measuring tube by means of changes in resistance. Since, in the absence of external forces acting on the measuring tube, a change in the periphery and/or in the axial extent of the measuring tube is dependent only on the pressure prevailing in the medium, it is possible by determining the peripheral stress and/or the axial stress of the measuring tube to also determine the pressure prevailing in the measuring tube, so that a pressure dependency of the density of the medium can also be taken into consideration or compensated.

In a particularly preferred exemplary embodiment of the method according to the invention, the mechanical stress of the measuring tube is measured in the non-deflected state of the measuring tube. By means of said measure, it can be ensured that those mechanical stresses which result from the deformation of the measuring tube caused by the vibration of the measuring tube are not taken into consideration; in the non-deflected state of the vibrating measuring tube, it is possible in a small time period to carry out a measurement of the mechanical stress free from dynamic effects and mechanical stress components caused by dynamic effects. If the vibrating measuring tube is not acted on by any other force, it is possible, in the instant of the non-deflected state, and by measuring the mechanical stress, to measure only those components of the stress which result, for example, from the pressure prevailing in the medium of the measuring tube. In one preferred embodiment of the method, this is obtained by synchronization of the measurement of the mechanical stress with the vibration of the measuring tube by means of phase regulation or follow-up synchronization, which is often referred to as phase-locked loop (PLL).

In a further embodiment of the method in which, in order to determine the density of the medium, both the peripheral stress and also the axial stress of the measuring tube are used, only the peripheral stress or only the axial stress of the measuring tube is actually determined by means of measurement, and the in each case other mechanical stress is calculated mathematically from the measured mechanical stress value and from parameters which determine physical-geometrical properties of the measuring tube. This is, for example, possible by utilizing the relationship, which is defined by the Poisson ratio, between relative thickness variation and relative length variation in the event of the action of an external force or stress on the measuring tube.

The above-described methods are realized in an embodiment of the invention in that the influence of the mechanical stress of the measuring tube and/or the influence of the pressure in the medium on the density of the medium are or is taken into consideration or compensated by using a closed mathematical model. In this exemplary embodiment, the relationship between the measured mechanical stress of the measuring tube and/or of the measured pressure in the medium of the measuring tube and the density of the medium is formulated in the manner of an equation by means of a mathematical model, for example, by means of purely algebraic conditional equations or else by means of a differential equation or a differential equation system.

In another exemplary embodiment of the invention, the influence of the mechanical stress of the measuring tube or the influence of the pressure in the medium of the measuring tube on the density of the medium is described by at least one parameter line obtained by means of measurement or a set of parameter lines which—depending on the number of independent variables—form a two-dimensional or multi-dimensional characteristic surface. Exemplary embodiments are also possible in which some of the dependencies of interest are taken into consideration by means of a mathematical model and other dependencies are taken into consideration on the basis of a measured characteristic curve.

It is known from practice that density measuring devices are subjected to an aging process which can also have the effect that, on account of parameters which vary over a long period of time, the relationship between the stress of the measuring tube and the pressure of the medium in the measuring tube and the density of the medium changes overall, so that in one advantageous embodiment of the method, in particular, the parameter line or map which is obtained by means of measurement is determined at predeterminable times by calibration and thereby updated, wherein it can be necessary, for this purpose, for the density measuring device to be operated in a well-defined predetermined state or a plurality of predetermined states (medium, pressure, temperature etc.).

In accordance with a further teaching of the invention, the previously derived and indicated object is achieved in the case of the device for density measurement on the basis of vibration analysis described in the introduction in that the evaluating unit is designed such that the evaluating unit can carry out one of the methods described above. One particularly advantageous embodiment of said device is provided if the device is a mass throughflow measuring unit which operates on the Coriolis principle and which brings with it, "from the factory," all the properties in order to also be able to carry out a density measurement.

In detail, there are now a plurality of possibilities for designing and refining the method for operating a density measuring device according to the invention and a device for density measurement of just said type. In this regard, reference is made to the following detailed description of the invention in conjunction with the accompanying drawings.

DETAILED DESCRIPTION OF THE INVENTION

Figure 1:
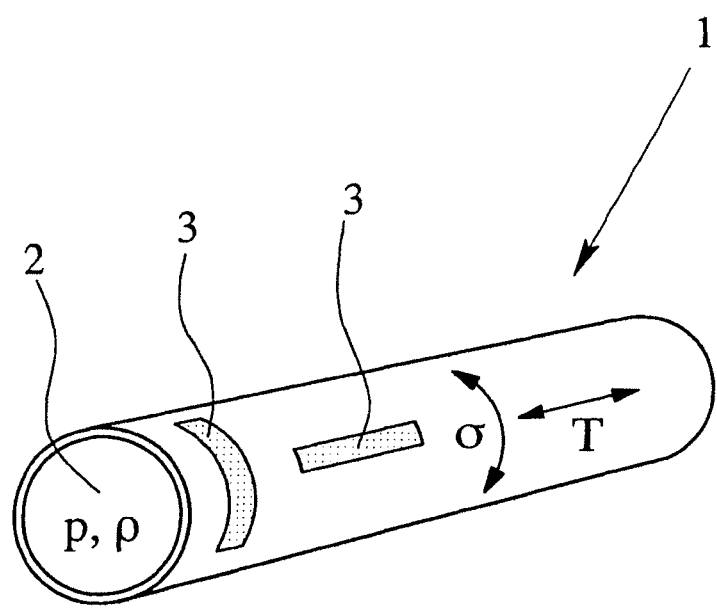
FIG. 1 is a schematic perspective view of a measuring tube having the most important parameters of interest.

FIG. 1 illustrates a measuring tube 1 as is provided in a density measuring device which is operated with a method for density measurement which is based on the evaluation of measurement tube vibrations. According to the method, the measurement tube 1 is, for this purpose, filled with a medium 2 and incited to vibrate. By determining the resulting frequency of the vibration, and by using other parameters which determine physical-geometrical properties of the measuring tube 1, the density $\rho$ of the medium 2 is then calculated.

The described calculation is based usually on a simple spring-mass model of the measuring tube 1 which is incited to vibrate, which spring-mass model is substantially dependent on the mass of the overall system and a single variable which characterizes the capability of vibration of the measuring tube. Such simple descriptions of the system which is capable of vibration are often insufficient descriptions of the actual conditions, since they do not take various influences into consideration. It has thus been recognized in the method illustrated in FIGS. 1 & 2 that the density $\rho$ of the medium 2 is not only a function of the frequency of the resulting natural vibration of the incited measuring tube 1 with constant parameters which describe geometrical-physical properties, but rather that the density $\rho$ of the medium 2 is also dependent on the mechanical stress of the measuring tube 1 and of the pressure p in the medium 2. Therefore, it is provided in accordance with the methods illustrated in FIGS. 1 & 2 that at least one mechanical stress of the measuring tube is determined, and with the obtained mechanical stress value, the influence of the mechanical stress of the measuring tube 1 and/or the influence of the pressure p in the medium 2 on the determined density $\rho$ of the medium 2 is taken into consideration or compensated.

Figure 2:
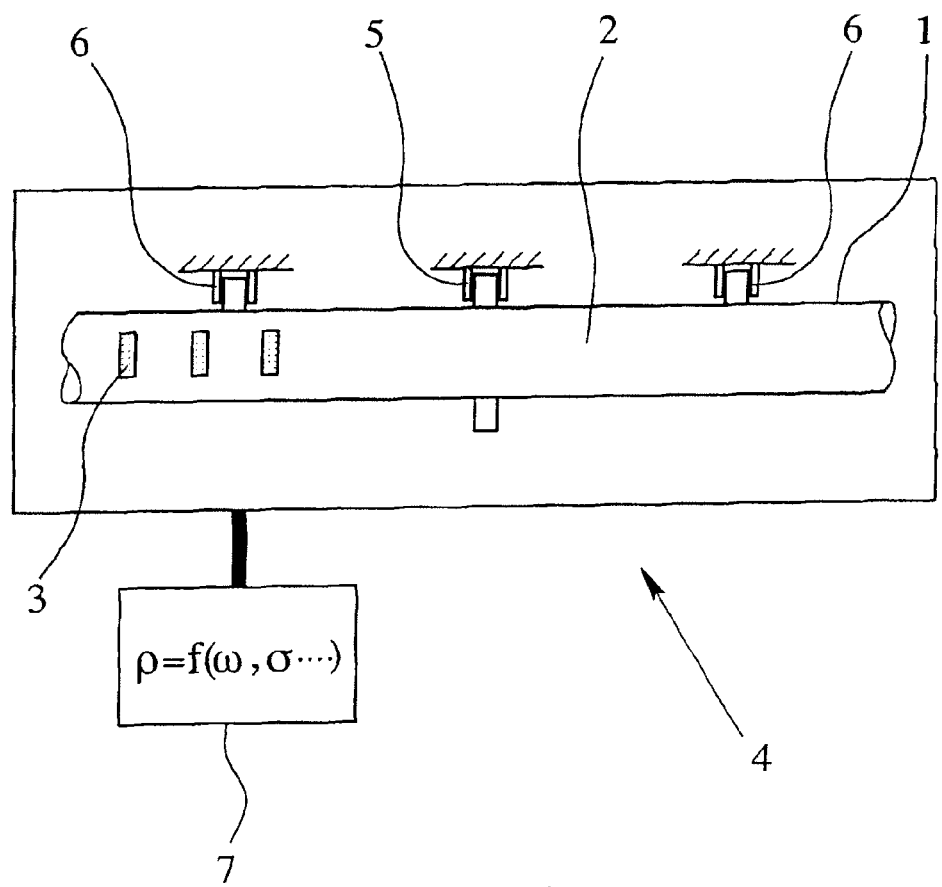
FIG. 2 is a schematic illustration of a device for density measurement.

In the exemplary embodiments illustrated in FIGS. 1 & 2, primarily the influence of the determined mechanical stress on the mechanical stiffness of the measuring tube 1 is taken into consideration or compensated. If it is taken into consideration that there is always a dependency between the mechanical stiffness of the measuring tube 1 and the density $\rho$ of the medium 2 even in the simplest mathematical-physical models (spring-mass system), then it is clear that, with the consideration of the influence of the determined mechanical stress on the mechanical stiffness of the measuring tube 1, at the same time, the influence of the determined mechanical stress on the density of the medium which is to be determined is also taken into consideration or compensated.

In the exemplary embodiment of FIG. 1, the peripheral stress $\sigma$ and the axial stress T are determined by measuring the mechanical stress using a respective strain gauge strip 3 for each stress. The resistance of the strain gauge strip 3 varies with the expansion and compression of the strain gauge strip 3 which resistance is determined by means of a Wheatstone bridge circuit (not illustrated). The strain gauge strips 3 are attached to the measuring tube 1 in such a way that they must directly follow changes in the periphery or in the axial extent of the measuring tube 1 and the compressions and extensions which are thus measured, permit a determination of the underlying stress changes in the peripheral direction and in the axial direction.

The peripheral stress $\sigma$ and the axial stress T of the measuring tube 1 are normal stresses which are aligned in each case perpendicular to a section face of the measuring tube casing of the measuring tube 1; in the case of the peripheral stress $\sigma$, the cross-sectional face is obtained by means of a section in the wall of the measuring tube which runs parallel to the longitudinal extent of the tube, and in the case of the axial stress T, the section face is obtained by means of a section through the wall of the measuring tube 1 which runs perpendicular to the longitudinal extent of the measuring tube 1. The mechanical stresses $\sigma$, T, therefore, have a particular significance for the determination of the density $\rho$ of the medium 2 within the measuring tube 1 because the mechanical stresses $\sigma$, T influence, in particular, the spring stiffness of the measuring tube 1, and therefore, the natural frequency with which the measuring tube 1 vibrates; in other words, the natural frequency of the vibration of the measuring tube 1 also varies, for an identical medium 2 which is assumed to be incompressible, when the pressure p within the medium 2 is varied without any change occurring in the density $\rho$ of the medium 2. This dependency is allowed for with the described and illustrated embodiment of the method.

In FIGS. 1 & 2, the method for operating the density measuring device is designed such that the mechanical stress $\sigma$, T of the measuring tube 1 is measured in the non-deflected state of the measuring tube 1, which is of particular interest because, in the non-deflected state of the measuring tube 1, the dynamic component—that is to say the component caused by the vibration of the measuring tube 1—of the mechanical stress $\sigma$, T has a zero crossing within the measuring tube 1 or within the wall of the measuring tube 1, that is to say substantially only the stress caused by the pressure p which acts within the medium 2 is noticeable. A targeted measurement of this type is brought about in the illustrated cases by synchronization of the measurement of the mechanical stress $\sigma$, T with the vibration of the measuring tube 1 by means of phase regulation or suitable follow-up synchronization; such types of regulation are conventionally referred to as "phase-locked loop" regulation.

In the method illustrated in FIG. 2, only the peripheral stress $\sigma$ is recorded by means of strain gauge strips 3, and the axial stress T within the measuring tube 1 is not taken into consideration for the correction of the calculated density value $\rho$ of the medium 2. In other, unillustrated, exemplary embodiments of the method, only the peripheral stress $\sigma$ or only the axial stress T of the measuring tube 1 is determined by means of measurement, and the respective other mechanical stress—that is to say the axial stress T or the peripheral stress $\sigma$—is calculated mathematically from the measured mechanical stress value $\sigma$, T and from parameters which determine physical-geometrical properties of the measuring tube 1. For example, the relationship between longitudinal expansion and transverse contraction (Poisson ratio) is additionally taken into consideration, so that from the one stress, the other stress can be determined.

In the case of the method illustrated in FIG. 1, the influence of the mechanical stress $\sigma$, T of the measuring tube 1 and the influence of the pressure p in the medium 2 on the density $\rho$ of the medium 2 is taken into consideration by using a closed mathematical model. This means that there is a formulaic relationship between the density ρ of the medium 2 of the measured frequency of the vibration of the measuring tube 1 and the measured mechanical stress σ, T, which takes into consideration precisely the influence of the mechanical stress, for example, on the stiffness of the measuring tube 1, so that overall—in comparison with the simplified model—a better result is obtained for the density value ρ of the medium 2 within the measuring tube 1. The same otherwise also applies to the method for density measurement illustrated in FIG. 2.

In another unillustrated embodiment of the invention, consideration of the influence of the mechanical stress σ, T of the measuring tube 1 on the density ρ of the medium 2 is not based on any analytical mathematical model, but rather a parameter line which is obtained by means of measurement and which reflects the relationship taken into consideration in the determination of the density ρ of the medium 2. The term "parameter line" is to be understood here, not in a restrictive fashion as merely a single curve which mediates between two different variables, but rather the term is to be understood more generally, so that said parameter line can also be a set of curves of parameter lines or, in the case of dependency of a plurality of variables, a two-dimensional or multi-dimensional parameter surface which, for example, assigns a specific starting value—density of the medium 2 within the measuring tube 1—to the variables of natural frequency of the vibration of the measuring tube 1, volume of the measuring tube 1, mechanical stresses of the measuring tube wall σ, T.

In the exemplary embodiments described above, the parameter line which is obtained by means of measurement or the characteristic map which is obtained by means of measurement or the multi-dimensional characteristic surface which is obtained is re-determined at predeterminable times by calibration, for which purpose the measuring tube 1 or the medium 2 within the measuring tube 1 must preferably be placed into determined, well-defined states.

FIG. 2 schematically illustrates an overall device 4 for density measurement on the basis of vibration analysis, with the device comprising a measuring tube 1, a medium 2 which is situated in the measuring tube 1, a vibration generator 5 which acts on the measuring tube 1, two measured value sensors 6 for measuring the vibration of the measuring tube 1, and an evaluating unit 7. The evaluating unit 7 serves for evaluating the vibration of the measuring tube 1 measured by the measured value sensors 6 and for calculating a density value ρ of the medium 2 from the measured vibration and other parameters which determine physical-geometrical properties of the measuring tube 1. To record the vibrations, strain gauge strips 3 are arranged on the measuring tube 1, which strain gauge strips 3 permit precise appraisal of the peripheral stress σ within the wall of the measuring tube 1. The evaluating unit 7 makes it possible to evaluate the vibration of the measuring tube 1 on the basis of the measured signals output by the measured value sensors 6 and also to measure the peripheral stress σ within the measuring tube on the basis of the signals provided by the strain gauge strips 3, and from the measured variables, to determine the density ρ of the medium 2 as a function of the obtained mechanical stress value σ and/or of the pressure p in the medium 2.

The device for density measurement on the basis of vibration analysis illustrated in FIG. 2 is a mass throughflow meter based on the Coriolis principle, with the central components of the Coriolis mass throughflow meter being schematically illustrated; for example, the measuring tube 1 is thus not illustrated completely up to the connecting flanges to the surrounding tube line system. A mass throughflow measuring unit operating on the Coriolis principle, fundamentally, brings with it the possibility of also carrying out a density measurement on the basis of vibration analysis of a medium 2 situated in the measuring tube.

What is claimed is:

1. A method for operating a density measuring device having a measuring tube for determining the density of a medium, comprising the steps of:
    filling a measuring tube with a medium,
    inciting the measuring tube to vibrate,
    determining the frequency of the vibration and other parameters which determine the physical-geometrical properties of the measuring tube,
    calculating the density of the medium from the determined frequency at least partially compensating for the influence of other parameters on the calculated density of the medium,
    wherein said other parameters comprise at least one of the pressure in the medium and at least one physical-geometrical property of the measuring tube, said at least one physical-geometrical property including at least one mechanical stress of the measuring tube,
    wherein the mechanical stress of the measuring tube is measured only in a non-deflected state of the measuring tube by synchronizing measurement of the mechanical stress with the frequency of the vibration determined, and
    wherein the influence of the mechanical stress on the calculated density is compensated using only the mechanical stress determined during the non-deflected state of the measuring tube.

2. The method as claimed in claim 1, wherein the influence of the determined at least one mechanical stress on the mechanical stiffness of the measuring tube on the density is compensated.

3. The method as claimed in claim 1, wherein said at least one mechanical stress comprises at least one of the peripheral stress and the axial stress of the tube.

4. The method as claimed in claim 1, wherein the mechanical stress is determined by being measured with at least one strain gauge strip.

5. The method as claimed in claim 1, wherein the value of only one of the peripheral stress and the axial stress of the measuring tube is determined by means of measurement, and the other the peripheral stress and the axial stress is calculated mathematically from the measured mechanical stress value and from parameters which determine physical-geometrical properties of the measuring tube.

6. The method as claimed in claim 1, wherein the influence of said other parameters is compensated by using at least one of a closed mathematical model and at least one parameter line obtained by means of measurement.

7. The method as claimed in claim 6, wherein a parameter line which is obtained by means of measurement is determined at predetermined times by calibration.

8. A device for density measurement on the basis of vibration analysis, comprising:
    at least one measuring tube with a medium situated therein,
    at least one vibration generator positioned to act on the at least one measuring tube,
    at least one measured value sensor for measuring vibration of the measuring tube,
    at least one other parameter measuring sensor, and
    an evaluating unit connected to receive signals from said sensors and adapted for calculating a density value of the medium from the measured vibration and other parameters, said other parameters comprising at least one of the pressure in the medium and at least one physical-geometrical property of the measuring tube, said at least one physical-geometrical property including at least one mechanical stress of the measuring tube, and wherein the evaluating unit is adapted for determining mechanical stress of the measuring tube only in a non-deflected state of the measuring tube by synchronizing measurement of the mechanical stress with the frequency of the vibration determined, and wherein the influence of the mechanical stress on the calculated density is compensated using only the mechanical stress determined during the non-deflected state of the measuring tube.

9. The device as claimed in claim 8, wherein said measuring tube, at least one vibration generator and at least one measured value sensor are parts of a Coriolis throughflow measuring unit.

* * * * *